United States Patent
Hsu et al.

(10) Patent No.: US 11,879,006 B2
(45) Date of Patent: Jan. 23, 2024

(54) RECOMBINANT ANTIBODY AND USES THEREOF

(71) Applicant: Academia Sinica, Taipei (TW)

(72) Inventors: Shang-Te Danny Hsu, Taipei (TW); Hui-Wen Chang, Taipei (TW); Chia-Yu Chang, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 17/851,277

(22) Filed: Jun. 28, 2022

(65) Prior Publication Data

US 2023/0037864 A1 Feb. 9, 2023

Related U.S. Application Data

(60) Provisional application No. 63/219,363, filed on Jul. 8, 2021.

(51) Int. Cl.
 *C07K 16/00* (2006.01)
 *C07K 16/10* (2006.01)
 *G01N 33/569* (2006.01)

(52) U.S. Cl.
 CPC ....... *C07K 16/10* (2013.01); *G01N 33/56983* (2013.01); *C07K 2317/565* (2013.01); *C07K 2317/622* (2013.01); *C07K 2317/76* (2013.01); *G01N 2333/17* (2013.01)

(58) Field of Classification Search
 CPC .............. C07K 16/10; C07K 2317/565; C07K 2317/622; C07K 2317/76; C07K 2317/56; G01N 2333/17
 See application file for complete search history.

(56) References Cited

PUBLICATIONS

Chang et al., "Generation and Characterization of a Spike Glycoprotein Domain A-Specific Neutralizing Single-Chain Variable Fragment against Porcine Epidemic Diarrhea Virus", Vaccines, MDPI, Jul. 29, 2021.

*Primary Examiner* — Lei Yao
(74) *Attorney, Agent, or Firm* — NZ CARR LAW OFFICE (57) ABSTRACT

Disclosed herein is a recombinant antibody exhibiting binding affinity and/or neutralizing activity to porcine epidemic diarrhea virus (PEDV). According to some embodiments of the present disclosure, the PEDV is genotype 1 (G1) or genotype 2b (G2b) PEDV. Also disclosed herein are methods of diagnosing and treating PEDV infection by use of the present recombinant antibody.

8 Claims, 2 Drawing Sheets

Specification includes a Sequence Listing.

RECOMBINANT ANTIBODY AND USES THEREOF

CROSS-REFERENCE TO RELATED APPLICATIONS

This application relates to and claims the benefit of U.S. Provisional Application No. 63/219,363, filed Jul. 8, 2021; the content of the application is incorporated herein by reference in its entirety.

STATEMENT REGARDING PRIOR DISCLOSURES BY THE INVENTOR OR A JOINT INVENTOR UNDER 37 C.F.R. 1.77(B)(6)

Most of the subject matter of the invention described in the present application was published by the inventors, Shang-Te Danny HSU, Hui-Wen CHANG, and Chia-Yu CHANG in an article titled "Generation and Characterization of a Spike Glycoprotein Domain A-Specific Neutralizing Single-Chain Variable Fragment against Porcine Epidemic Diarrhea Virus." The article was published in Vaccines, 2021, 9: 833 on Jul. 29, 2021. Therefore, the publication was made by and/or originated from all member of the inventive entity of the present invention less than one year before the filing date of the present application. A copy of the article is provided in a concurrently filed Information Disclosure Statement pursuant to the guidance of 78 Fed. Reg. 11076 (Feb. 14, 2013).

BACKGROUND OF THE INVENTION

1. Field of the Invention

The present disclosure in general relates to the field of diagnosing and treating viral infection. More particularly, the present disclosure relates to a novel recombinant antibody and the uses thereof in the diagnosis and treatment of porcine epidemic diarrhea virus (PEDV) infection.

2. Description of Related Art

Porcine epidemic diarrhea virus (PEDV) is a contagious swine enteric virus that causes porcine epidemic diarrhea (PED) in neonatal and suckling piglets, and impacts the swine industry all over the world. The historic genotype 1 (G1; also known as low-pathogenic genotype) PEDV was first identified in late 1970s in Belgium and subsequently became an endemic disease over the past decades in Europe and Asia with sporadically outbreaks. A new variant of PEDV, which belongs to genotype 2 (G2; also known as high-pathogenic genotype, including local epidemic G2a, and global epidemic or pandemic G2b) based on the phylogenetic analysis, has emerged since 2010 in China, and rapidly spread across North America and Asia. This new PEDV variant caused a high morbidity and a high mortality in neonatal piglets. Up to the present time, there is no agent available to effectively treat and control seasonal outbreaks of PED in neonatal piglets.

In view of the foregoing, there exists in the related art a need for a novel agent for treating PEDV infection so as to minimize the impact of PEDV on swine health and production.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

As embodied and broadly described herein, one aspect of the disclosure is directed to a recombinant antibody for the diagnosis and/or treatment of PEDV infection. The recombinant antibody comprises a light chain variable (VL) domain and a heavy chain variable (VH) domain, in which the VL domain comprises a first light chain complementarity determining region (CDR-L1), a second light chain CDR (CDR-L2), and a third light chain CDR (CDR-L3); and the VH domain comprises a first heavy chain CDR (CDR-H1), a second heavy chain CDR (CDR-H2), and a third heavy chain CDR (CDR-H3).

According to some embodiments of the present disclosure, the CDR-L1 comprises the amino acid sequence of "ENVGTY" (SEQ ID NO: 1), the CDR-L2 comprises the amino acid sequence of "GTF", and the CDR-L3 comprises the amino acid sequence of "GQSYNYPFT" (SEQ ID NO: 2). In these embodiments, the CDR-H1 comprises the amino acid sequence of "GYTFTNYM" (SEQ ID NO: 3), the CDR-H2 comprises the amino acid sequence of "INPSTGYT" (SEQ ID NO: 4), and the CDR-H3 comprises the amino acid sequence of "ATSTLITGDY" (SEQ ID NO: 5).

According to certain preferred embodiments, the VL domain comprises an amino acid sequence at least 85% identical to SEQ ID NO: 6, and the VH domain comprises an amino acid sequence at least 85% identical to SEQ ID NO: 7. In one specific example, the VL domain comprises an amino acid sequence 100% identical to SEQ ID NO: 6, and the VH domain comprises an amino acid sequence 100% identical to SEQ ID NO: 7.

According to certain embodiments, the recombinant antibody is a single-chain variable fragment (scFv). Preferably, the recombinant antibody further comprises a linker connecting the VL domain and the VH domain. According to some embodiments, the linker comprises the amino acid sequence of (GGGGS)$_3$ (SEQ ID NO: 8).

The second aspect of this disclosure is directed to a method of diagnosing whether a subject is infected by PEDV via a biological sample isolated from the subject. The method comprises the step of detecting the presence or absence of a spike (S) protein of the PEDV in the biological sample by use of the recombinant antibody of the present disclosure, wherein the presence of the S protein indicates that the subject is infected by the PEDV.

According to some embodiments, the PEDV is G1 PEDV. According to certain embodiments, the PEDV is G2b PEDV.

Depending on desired purposes, the biological sample may be a blood sample (e.g., a whole blood sample, a serum sample or a plasma sample), an oral sample, an intestinal sample, a rectal sample or a fecal sample.

Also disclosed herein is a method of treating PEDV infection in a subject. The present method comprises administering to the subject an effective amount of the recombinant antibody of the present disclosure.

According to some embodiments, the PEDV is G2b PEDV.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where:

FIG. 2 are photographs depicting cytopathic effects (CPEs) in neutralization test according to Example 4 of the present disclosure. The recombinant scFv was incubated with 400 $TCID_{50}$/mL PEDV-PT (G2b PEDV) for 2 hours and then subjected to Vero cells. The CPE was observed every 24 hours to determine the neutralizing ability of the present scFv. The images were taken at the end time point, 72 hours. Panel A: Cells infected by virus and treated with 25 μg/mL recombinant scFv. Panel B: Challenge control group, in which cells were infected by virus without recombinant scFv treatment. Panel C: Non-challenged control group, in which cells were treated with phosphate buffered saline (PBS; i.e., no virus infection and no recombinant scFv treatment). The black bars represented 100 μm in length.

DETAILED DESCRIPTION OF THE INVENTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

I. Definition

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The term "antibody" is used in the broadest sense and specifically covers monoclonal antibodies (including full length monoclonal antibodies), polyclonal antibodies, multispecific or multivalent antibodies (e.g., bi-specific antibodies), and antibody fragments so long as they exhibit the desired biological activity. An "antibody fragment" comprises a portion of a full-length antibody, generally the antigen binding or variable region thereof. Examples of antibody fragment include fragment antigen-binding (Fab), Fab', F(ab')2, single-chain variable fragment (scFv), diabody, linear antibody, single-chain antibody molecule, and multi-specific antibody formed from antibody fragment. According to some working embodiments, the antibody is an scFv.

As used herein, the term "single-chain variable fragment" or "scFv" is a fusion protein comprising the variable regions of the heavy (VH) and light chains (VL) of an immunoglobulin, in which the VH and VL are covalently linked to form a VH-VL heterodimer. The VH and VL are either joined directly or joined by a peptide-encoding linker, which connects the N-terminus of the VH with the C-terminus of the VL, or the C-terminus of the VH with the N-terminus of the VL. The linker is usually rich in glycine for flexibility, as well as serine or threonine for solubility. Despite removal of the constant regions and the introduction of a linker, scFv proteins retain the specificity of the original immunoglobulin. ScFv polypeptide antibodies can be expressed from a nucleic acid including VH- and VL-encoding sequences.

The "variable region" or "variable domain" of an antibody refers to the amino-terminal domains of heavy or light chain of the antibody. These domains are generally the most variable parts of an antibody and contain the antigen-binding sites. The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen-binding site of antibodies. The constant domains are not involved directly in binding an antibody to an antigen, but exhibit various effector functions, such as participation of the antibody in antibody-dependent cellular toxicity.

The term "complementarity determining region" (CDR) used herein refers to the hypervariable region of an antibody that forms a surface complementary to the 3-dimensional surface of a bound antigen. Proceeding from N-terminus to C-terminus, each of the antibody heavy and light chains comprises three CDRs (i.e., CDR-L1, CDR-L2 and CDR-L3 in the light chain, and CDR-H1, CDR-H2 and CDR-H3 in the heavy chain). An HLA-DR antigen-binding site, therefore, includes a total of six CDRs that comprise three CDRs from the variable region of a heavy chain and three CDRs from the variable region of a light chain.

As discussed herein, minor variations in the amino acid sequences of antibodies are contemplated as being encompassed by the presently disclosed and claimed inventive concept(s), providing that the variations in the amino acid sequence maintain at least 85% sequence identity, such as at least 85%, 86%, 87%, 88%, 89%, 90%, 91%, 92%, 93%, 94%, 95%, 96%, 97%, 98% and 99% sequence identity. Antibodies of the present disclosure may be modified specifically to alter a feature of the peptide unrelated to its physiological activity. For example, certain amino acids can be changed and/or deleted without affecting the physiological activity of the antibody in this study (i.e., its ability to determine and/or treat PEDV infection). In particular, conservative amino acid replacements are contemplated. Conservative replacements are those that take place within a family of amino acids that are related in their side chains. Genetically encoded amino acids are generally divided into families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the peptide derivative. Fragments or analogs of antibodies can be readily prepared by those of ordinary skill in the art. Preferred amino- and carboxyl-termini of fragments or analogs occur near boundaries of functional domains. In one example, one amino acid residue (e.g., valine) of the present antibody is conservatively replaced (e.g., by leucine). In other examples, two amino acid residues of the present antibody are conservatively replaced by other suitable amino acid residues, for example, valine (V) and arginine (R) are replaced by the pair of amino acids that includes, but is not limited to, methionine (M) and lysine (K), lysine (K) and proline (P), tryptophan (W) and isoleucine (I), isoleucine (I) and proline (P), asparagine (N) and valine (V), and glutamine (G) and lysine (K).

"Percentage (%) sequence identity" is defined as the percentage of amino acid residues in a candidate sequence that are identical with the amino acid residues in the specific peptide sequence, after aligning the sequences and introducing gaps, if necessary, to achieve the maximum percent sequence identity, and not considering any conservative substitutions as part of the sequence identity. Alignment for purposes of determining percentage sequence identity can be achieved in various ways that are within the skill in the art, for instance, using publicly available computer software such as BLAST, BLAST-2, ALIGN or Megalign (DNAS-TAR) software. Those skilled in the art can determine appropriate parameters for measuring alignment, including any algorithms needed to achieve maximal alignment over the full length of the sequences being compared. For purposes herein, sequence comparison between two amino acid sequences was carried out by computer program Blastp (protein-protein BLAST) provided online by Nation Center for Biotechnology Information (NCBI). The percentage amino acid sequence identity of a given amino acid sequence A to a given amino acid sequence B (which can alternatively be phrased as a given amino acid sequence A that has a certain % amino acid sequence identity to a given amino acid sequence B) is calculated by the formula as follows:

$$\frac{X}{Y} \times 100$$

where X is the number of amino acid residues scored as identical matches by the sequence alignment program BLAST in that program's alignment of A and B, and where Y is the total number of amino acid residues in A or B, whichever is shorter.

The term "effective amount" as referred to herein designate the quantity of a component which is sufficient to yield a desired response. For therapeutic purposes, the effective amount is also one in which any toxic or detrimental effects of the component are outweighed by the therapeutically beneficial effects. The specific effective or sufficient amount will vary with such factors as the particular condition being treated, the physical condition of the subject (e.g., the subject's body mass or age), the duration of the treatment, the nature of concurrent therapy (if any), and the specific formulations employed and the structure of the compounds or its derivatives. Effective amount may be expressed, for example, in grams, milligrams or micrograms or as milligrams per kilogram of body weight (mg/Kg). Alternatively, the effective amount can be expressed in the concentration of the active component (e.g., the present recombinant antibody), such as molar concentration, mass concentration, volume concentration, molality, mole fraction, mass fraction and mixing ratio.

As used herein, the term "treat," "treating" and "treatment" are interchangeable, and encompasses partially or completely preventing, ameliorating, mitigating and/or managing a symptom, a secondary disorder or a condition associated with PEDV infection. The term "treating" as used herein refers to application or administration of the recombinant antibody of the present disclosure to a subject, who has a symptom, a secondary disorder or a condition associated with PEDV infection, with the purpose to partially or completely alleviate, ameliorate, relieve, delay onset of, inhibit progression of, reduce severity of, and/or reduce incidence of one or more symptoms, secondary disorders or features associated with PEDV infection. Symptoms, secondary disorders, and/or conditions associated with PEDV infection include, but are not limited to, diarrhea, vomiting, 
dehydration, the loss of appetite, anorexia and depression. Treatment may be administered to a subject who exhibits only early signs of such symptoms, disorder, and/or condition for the purpose of decreasing the risk of developing the symptoms, secondary disorders, and/or conditions associated with PEDV infection. Treatment is generally "effective" if one or more symptoms or clinical markers are reduced as that term is defined herein. Alternatively, a treatment is "effective" if the progression of a symptom, disorder or condition is reduced or halted.

The term "subject" refers to a swine that is suitable to be diagnosed or treated with the recombinant antibody and/or methods of the present invention. The term "subject" is intended to refer to both the male and female gender unless one gender is specifically indicated.

II. Description of the Invention

The present disclosure aims at providing a recombinant antibody for detecting and/or treating PEDV infection so as to minimize the impact of disease for the industry. Accordingly, the first aspect of the present disclosure is directed to a recombinant antibody, which exhibits binding and neutralizing activities to PEDV, e.g., G1 PEDV or G2b PEDV. According to embodiments of the present disclosure, the recombinant antibody comprises a VL domain and a VH domain, in which the VL domain comprises CDR-L1, CDR-L2 and CDR-L3, and the VH domain comprises CDR-H1, CDR-H2 and CDR-H3. In these embodiments, the CDR-L1, CDR-L2 and CDR-L3 of the recombinant antibody respectively comprise the amino acid sequences of "ENVGTY" (SEQ ID NO: 1), "GTF", and "GQSYNYPFT" (SEQ ID NO: 2); and the CDR-H1, CDR-H2 and CDR-H3 of the recombinant antibody respectively comprise the amino acid sequences of "GYTFTNYM" (SEQ ID NO: 3), "INPSTGYT" (SEQ ID NO: 4), and "ATSTLITGDY" (SEQ ID NO: 5).

Preferably, the VL domain of the recombinant antibody comprises an amino acid sequence at least 85% (i.e., 85%, 86%, 87%, 88%, 89%, 90%, 91%, 92%, 93%, 94%, 95%, 96%, 97%, 98%, 99% or 100%) identical to SEQ ID NO: 6, and the VH domain of the recombinant antibody comprises an amino acid sequence at least 85% (i.e., 85%, 86%, 87%, 88%, 89%, 90%, 91%, 92%, 93%, 94%, 95%, 96%, 97%, 98%, 99% or 100%) identical to SEQ ID NO: 7. As could be appreciated, the framework sequences of the VL and VH domains may vary (e.g., being substituted by conserved or non-conserved amino acid residues) without affecting the binding affinity and/or specificity of the present antibody. Preferably, the amino acid residue of the framework sequence is conservatively substituted by one or more suitable amino acid(s) with similar properties; for example, the substitution of leucine (an nonpolar amino acid residue) by isoleucine, alanine, valine, proline, phenylalanine, or tryptophan (another nonpolar amino acid residue); the substitution of aspartate (an acidic amino acid residue) by glutamate (another acidic amino acid residue); or the substitution of lysine (an basic amino acid residue) by arginine or histidine (another basic amino acid residue). According to the preferred embodiment, the VL and VH domains respectively comprise amino acid sequences at least 90% identical to SEQ ID NOs: 6 and 7. More preferably, the VL and VH domains respectively comprise amino acid sequences at least 95% identical to SEQ ID NOs: 6 and 7. In one working example of the present disclosure, the VL domain comprises the amino acid sequence 100% identical to SEQ ID NO: 6 (i.e., comprising the amino acid sequence of SEQ ID NO: 6), and the VH domain comprises the amino acid sequence 100% identical to SEQ ID NO: 7 (i.e., comprising the amino acid sequence of SEQ ID NO: 7).

According to some embodiments of the present disclosure, the recombinant antibody is produced in the form of scFv, which optionally further comprises a linker connecting the VL and VH domains. According to some embodiments, the recombinant antibody comprises the VL domain, the linker and the VH domain, from N-terminus to C-terminus, in sequence. According to alternative embodiments, the recombinant antibody comprises the VH domain, the linker and the VL domain, from N-terminus to C-terminus, in sequence. Preferably, the linker comprises glycine (G) and/or serine (S) residues. More preferably, the linker consists of G and/or S residues. In one specific example, the linker comprises the amino acid sequence of $(GGGGS)_3$ (SEQ ID NO: 8).

According to certain embodiments, the recombinant antibody of the present disclosure is derived from a monoclonal antibody produced by conventional immunization method (i.e., immunizing animals with a suitable antigen).

The method of immunizing animal to generate antibody is known by a person having ordinary skill in the art. In general, a viral particle (e.g., PEDV viral particle) serving as an immunogen is peritoneally or subcutaneously injected to a host animal, such as a mouse, a rat, or a rabbit, to stimulate an immune response in the host animal. According to some embodiments of the present disclosure, the host animal for generating the monoclonal antibody is a mouse. The immunization may be performed in accordance with commonly adopted procedures. The immunization interval is not particularly limited. Immunization may be carried out at intervals of several days to several weeks, preferably one week, for 2-10 times, until a desired antibody titer is reached. For example, the host animals may be vaccinated by subcutaneously injecting with the viral particle on weekly basis for 8 consecutive weeks.

Blood samples are taken regularly after immunization and subjected to centrifugation to separate sera. The resultant sera are then subject to measurement of antibody titers by any suitable method, which includes, but is not limited to, ELISA, enzyme immunoassay (EIA), or radio immunoassay (MA). In one preferred example, antibody titers are measured by ELISA. Then, final immunization is given to those animals showing high antibody titers to the viral particle. Antibody-producing cells are prepared from splenic cells and regional lymph nodes or the like of the immunized animals. In the preparation of antibody-producing cells, it is preferably to remove tissue debris and erythrocytes as much as possible. Commercial erythrocyte remover may be used to this purpose. Alternatively, a buffer ammonium chloride and tris(hydroxymethyl)aminomethane (Tris) may be prepared and used. The thus-prepared antibody-producing cells should be immediately fused with immortal cells such as myeloma cells to produce hybridoma cells, which semi-eternally continue to proliferate while producing antibodies. Commonly available cell strain derived from an animal such as mouse may be used. A preferable cell strain to be used in this invention should not survive in HAT selection medium, which contains hypoxanthine, thymidine and aminopterin; and should survive there only when fused with antibody-producing cells. Examples of myeloma cells include, but are not limited to, mouse myeloma cell line (such as myeloma FO cells) and human myeloma cell line (such as Karpas 707H). Cell fusion is usually carried out by mixing splenic cells or lymph node cells with commercial available myeloma cells in the presence of a cell-fusion promoter, such as polyethylene glycol (PEG) having an average molecular weight from about 200 to 20,000 daltons or the like. Alternatively, cell fusion may be carried out in a commercial cell fusion device utilizing electric stimulation such as electroporation. After the fusion, the resultant cells are then diluted and cultured in HAT medium.

Hybridomas of interest are then selected from the fused cells. The fused cells surviving cultured in HAT medium would form colonies. The supernatant of each culture well is then collected and examine for the presence or absence of antibody titers to the viral particle. As a method of confirmation, ELISA, EIA or RIA may be used. Once antibody-positive wells are identified, cells are then cultured in an HT medium, which does not contain aminopterin. After culturing for a while, antibody titers in the culture supernatant are confirmed again. Cells that are finally selected are then subject to cloning to obtain single cells. Clones that exhibit high specificity to the viral particle are selected, and are proliferated to some extent to establish hybridomas.

According to some embodiments of the present disclosure, the thus-obtained hybridoma is subjected to a nucleic acid extraction method, e.g., organic extraction; the isolated nucleic acid then serves as a template to amplify the VL and VH domains of the recombinant antibody by polymerase chain reaction (PCR) with codon-optimizing primers (i.e., the primers listed in Table 1). The amplified sequences are cloned into an expression vector, which is then transfected into host cells, such as *E. coli* cells or mammalian cells (e.g., human 293T cells or Chinese hamster ovary (CHO) cells) to produce the recombinant antibody of the present disclosure. According to preferred embodiments, the recombinant antibody is produced by mammalian cells. In one specific example, the recombinant antibody is produced by human 293T cells.

Once produced, the recombinant antibody may be purified according to standard procedures in the art, including cross-flow filtration, affinity column chromatography, gel filtration and the like.

According to some embodiments of the present disclosure, the recombinant antibody is useful in detecting PEDV infection in a biological sample via any detection technique known to a person having ordinary skill in the art, such as immunostaining (e.g., ICC and IFA), ELISA, western blotting, and flow cytometry.

The second aspect of the present disclosure thus pertains to a method of diagnosing whether a subject is infected by PEDV via a biological sample isolated from the subject by use of the recombinant antibody. The method comprises detecting the presence or absence of a spike (S) protein of the PEDV in the biological sample by use of the recombinant antibody, wherein the presence of the S protein indicates that the subject is infected by the PEDV.

According to certain embodiments, the PEDV is G1 PEDV. According to alternative embodiments, the PEDV is G2b PEDV.

Depending on desired purposes, the biological sample may be a blood sample (e.g., a whole blood sample, a serum sample or a plasma sample), an oral sample (e.g., oral fluid or buccal swab), an intestinal sample, a rectal sample or a fecal sample.

Also disclosed herein is a method of preventing and/or treating PEDV infection in a subject. The method comprises administering to the subject an effective amount of the recombinant antibody of the present disclosure.

The effective dose administered to the subject is from about 0.01 to 1,000 mg/Kg body weight of the subject, such as 0.01, 0.02, 0.03, 0.04, 0.05, 0.06, 0.07, 0.08, 0.09, 0.1, 0.2, 0.3 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 200, 250, 300, 350, 400, 450, 500, 550, 600, 650, 700, 750, 800, 850, 900, 950, or 1,000 mg/Kg body weight of the subject; preferably, about 0.1 to 100 mg/Kg body weight of the subject. The dose can be administered in a single aliquot, or alternatively in more than one aliquot. A skilled artisan may adjust the dosage or regime in accordance with the physical condition of the subject or the severity of the diseases.

The recombinant antibody may be administered to the subject by a suitable route; for example, oral, enteral, nasal, topical, transmucosal, and parenteral administration (e.g., intravenous, intraperitoneal or intraarterial injection). According to some preferred embodiments, the recombinant antibody is orally administered to the subject.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLES

Materials and Methods
Preparation of the Present Recombinant scFv

To prepare the present recombinant scFv, a hybridoma originating from PEDV viral particle-immunized mice was obtained in accordance with the immunization procedure known in the art. After confirming the binding affinity and specificity of the antibody produced by the hybridoma to PEDV, the mRNA was extracted from the corresponding hybridoma, and served as a template for amplifying the VL and VH domains of the antibody by using universal custom forward primer (ISPCR) and chain-specific reverse primers (Table 1). For each reaction, 2 μL cDNA, 10 μL PCR mixture, 1 μL 10 mM universal forward primer, 1 μL 10 mM chain-specific reverse primer, and 6 μL of PCR-grade water were prepared. The condition of thermal cycler was defined as follows: 94° C. for 3 minutes, 12 cycles of 95° C. for 30 seconds, 60° C. for 30 seconds (−0.5° C. per cycle), and 72° C. for 1 minute; and directly followed by 18 cycles of 95° C. for 30 seconds, 56° C. for 30 seconds, and 72° C. for 1 minute. The final extension was 5 minutes at 72° C. The expected sizes of amplicon were all approximately 550-600 bp. The sequences were analyzed to verify the framework regions (FRs) and the complementarity determining regions (CDRs) of each chain.

TABLE 1

Primers for amplifying VL and VH domains of the recombinant scFv

| Name | Primer sequence (from 5'-end to 3'-end) | SEQ ID NO |
|---|---|---|
| ISPCR | AAGCAGTGGTATCAACGCAGAG | 9 |
| mIgK reverse primer | ACATTGATGTCTTTGGGGTAGAAG | 10 |

TABLE 1-continued

Primers for amplifying VL and VH domains of the recombinant scFv

| Name | Primer sequence (from 5'-end to 3'-end) | SEQ ID NO |
|---|---|---|
| mIgL reverse primer | ATCGTACACACCAGTGTGGC | 11 |
| mIgHG reverse primer | GGGATCCAGAGTTCCAGGTC | 12 |

* ISPCR: common forward primer; mIgK: variable kappa light chain; mIgL: variable lambda light chain; mIgHG: variable heavy chain.

The amplified VL and VH sequences were cloned into expression vector pcDNA™3.1/V5-His TOPO. For the purposes of expression in mammalian cells, a $(G_4S)_3$ linker (SEQ ID NO: 8) was introduced between the VL and VH sequences, and a tissue plasminogen activator (tPA) signal sequence was introduced at the 5' end of the coding sequence to facilitate the secretory process. After ligation, the plasmid was amplified by competent *Escherichia coli* (*E. coli*), and then extracted by plasmid extraction kit. To transfect 1 L of EXPI293F™ cells at a concentration of 3×10⁶ cells/mL, 2.7 mL of transfection reagent was pre-diluted in 50 mL of OPTI-MEM® and mixed with 1 mg of the DNA plasmid pre-diluted in 50 mL of OPTIMEM®. The mixture was incubated at room temperature for 20 minutes prior to transfection. After adding the transfection mixture, the EXPI293F™ cells were cultured at 37° C., supplemented with 8% $CO_2$ with constant shaking at 125 rpm. At the end of the four-day transient expression, the supernatant and cell lysates of EXPI293F™ cells were collected for SDS-PAGE and western blotting analyses to confirm the expression level of the present scFv.

The thus-obtained recombinant scFv comprised the VL and VH domains. As summarized in Table 2, the VL and VH domains respectively comprise the amino acid sequences of SEQ ID NOs: 6 and 7, in which the CDR-L1, CDR-L2 and CDR-L3 respectively comprised the amino acid sequences of "ENVGTY" (SEQ ID NO: 1), "GTF", and "GQSYN-YPFT" (SEQ ID NO: 2), and the CDR-H1, CDR-H2 and CDR-H3 respectively comprised the amino acid sequences of "GYTFTNYM" (SEQ ID NO: 3), "INPSTGYT" (SEQ ID NO: 4), and "ATSTLITGDY" (SEQ ID NO: 5).

TABLE 2

Amino acid sequences of the VL and VH domains of the recombinant scFv

| Domain | Amino acid sequence | SEQ ID NO |
|---|---|---|
| VL | MDAMKRGLCCVLLLCGAVFVSPSASNIVLTQSPKS MSMSVGERVTLSCKASENVGTYVSWYQQKPKQSPK LLIYGTFNRYTGVPDRFTGSGSATDFTLTISSVQA EDLADYHCGQSYNYPFTFGSGTKLEIK | 6 |
| VH | QVQLQQSGAELARPGTSVKMSCKASGYTFTNYMMH WIKQRPGQGLEWIGYINPSTGYTNYNQKFKDKATL TADKSSSTAYVQLNILTSEDSAVYYCATSTLITGD YWGQGTTLTVSSKGQDNSAG | 7 |

* The CDR sequences were marked in boldface, including three CDRs (i.e., CDR-L1, CDR-L2 and CDR-L3, from N-terminus to C-terminus, in sequence) in the VL domain, and three CDRs (i.e., CDR-H1, CDR-H2 and CDR-H3, from N-terminus to C-terminus, in sequence) in the VH domain.

Purification of Recombinant scFv by Using Immobilized Metal Affinity Chromatography (IMAC) and Size Exclusion Chromatography (SEC)

After filtration by using a 0.22 µm filter cup, the supernatant was mixed with the binding buffer (500 mM Tris-HCl, 1.5 M sodium chloride, and 50 mM imidazole, pH 7.8) with a ratio of 10:1. The resin pre-washed with sterile water and TBA buffer (50 mM Tris-HCl, 150 mM sodium chloride, 0.02% sodium azide, pH7.6) was added to the supernatant in binding buffer in the ratio of 1:100. After overnight incubation at 4° C. with regular stirring, the resin was collected by column, and washed by wash buffer (20 mM Tris-HCl, 300 mM sodium chloride, and 10 mM imidazole, pH7.6). The target protein was eluted by using the elution buffer (20 mM Tris-HCl, 300 mM sodium chloride, and 150 mM imidazole, pH7.8). The eluent was concentrated to 0.5 ml for further purification in PBS by using an SUPERDEX™ 75 increase column coupled to a FPLC system.

Validation of Recombinant scFv by ICC and IFA

Vero cells were seeded on 96-well plates one day before challenge. The cells were washed with Dulbecco's phosphate-buffered saline (dPBS) and inoculated with 100 µL 500 $TCID_{50}$/mL of PEDV-PT passage 5 (G2b PEDV) or PEDV-CV777 (G1 PEDV) diluted in the TPA medium, a DMEM-based medium supplemented with 0.3% tryptose phosphate broth, 0.02% yeast extract, and 10 µg/mL trypsin. At the presence of visible CPE, the cells were fixed with 80% acetone for 20 minutes and air-dry for another 30 minutes. After washing with PBS for three times, the purified scFv was diluted to 5 µg/mL with PBS and applied to the wells for an hour incubation. To verify the signals, a blank filled with PBS was included as a background control. Following three washing steps with PBS, the 1,000× diluted anti-V5 antibody was used for another hour of incubation to probe the V5 tag on the recombinant scFv. The goat-anti-mouse IgG conjugated with horseradish peroxidase (HRP) or fluorescein isothiocyanate (FITC) were utilized as the secondary antibody and was incubated with the plates for 1 hour. Sequentially, the signals brining by HRP- or FITC-conjugated secondary antibody was detected.

Binding Affinity of Recombinant scFv to Homogenous and Heterogeneous PEDV Virions by Indirect ELISA The purified virions of PEDV-PT and PEDV-CV777 were diluted to 2 µg/mL with coating buffer followed by respectively coating onto the strips at 4° C. overnight. The strips were washed with 200 µL washing buffer for six times and sequentially blocked with 300 µL blocking buffer for 1 hour. The recombinant scFv were serially two-fold diluted from 20 µg/mL to 1.25 µg/mL, and applied on the strips under the condition of 100 uL/well, and incubated for 1 hour at room temperature. After washing with 200 µL of washing buffer for six times, the 1,000× diluted anti-V5 antibody was incubated with the strips for another hour to probe the V5 tag on the scFv. Following six times washing steps as mentioned above, the 1,000× diluted goat-anti-mouse IgG HRP was incubated with the strips for 1 hour. Fifty microliters of ABTS® peroxidase substrate were added after the strips were completely washed, and the coloration step was stopped by providing 50 µL stopping solution. The signals were detected at 405 nm by using the microplate reader.

Binding Affinity of Recombinant scFv to Purified PEDV S Protein by Using Immunoprecipitation Assay The ectodomain of the S protein of PEDV (GeneBank no. HC070225-S), hereafter as "PEDV S protein", has been constructed, expressed in HEK293 cells in a secreted form, and purified from the culture medium. To conduct the immunoprecipitation pull-down assay, 25 pmol of PEDV S protein (700 kDa in molecular weight as a homotrimer) was mixed with 125 pmol of scFv (30 kDa in molecular weight), and then incubated at 37° C. for three hours with regular shaking. A negative control of scFv only without the PEDV S protein was included. After incubation, the mixture was filtrated by a 100 kDa molecular weight cut-off (MWCO) spin column with centrifugation under 11,000 g for 5 minutes. The flow through was discarded and the column was washed with 10 column volumes (400 μL/per wash, ten washes) of dPBS to remove the unconjugated scFv. The mixture was concentrated to 100 μL after washing and analyzed by SDS-PAGE. 13 μL of concentrated mixture was mixed with 2 μL of 10× reducing agent and 5 μL of 5× sampling buffer, followed by thermal denaturation at 95° C. for 5 minute before applying to the 10% SDS-PAGE and stained with coomassie brilliant blue.

Estimation of Binding Affinity Between Recombinant scFv and PEDV S Protein by SEC The binding affinity of the scFv toward the PEDV S protein was estimated by SEC. In brief, 380 pmol of PEDV S protein was mixed with 830 pmol scFv, and incubated at room temperature for 1 hour. The mixture was filtered by a 0.22 μm spin column before being separated by a SUPER-OSE® 6 10/300 GL column in TBA buffer coupled to a FPLC System. The protein sample was monitored by the UV absorbance at 280 nm ($UV_{280}$) and fractionated with 0.5 mL per fraction. The fractions that should significant $UV_{280}$ absorbance were analyzed by western blotting. The proteins were denatured by adding 2 μL of 10× reducing agent and 5 μL of 5× sampling buffer, and then boiled at 95° C. for 5 minutes. The protein samples were separated by a 10% SDS-PAGE separating gel and transferred to a polyvinylidene difluoride (PVDF) membrane. The membrane was blocked with 5% skim milk for 30 minutes, and probed with 1:5,000 diluted anti-V5 tag antibody for 1 hour at room temperature. After thorough washing, the 1:10,000 diluted anti-mouse IgG antibody with HRP conjugation was added. After 1 hour of incubation and adequate washing, the V5-tag-positive protein signals were detected by using western blotting substrate and visualized by imaging system.

Neutralizing Test

Vero cells were maintained in the DMEM medium supplied with 10% FBS and antibiotic-antimycotic, and were seeded on the 96-well cell culture plates to reach the 90% confluency on the following day. The purified scFv was two-fold serially diluted from 25 μg/mL to 0.78 μg/mL in the TPA medium and mixed with constant 200 $TCID_{50}$/mL PEDV-PT-passage 5 or PEDV-CV777 strain. The controls without adding scFv (the diluted virus only) and without treatment (normal cells fed in TPA medium) were also included in both assays. The virus-antibody mixtures were incubated at 37° C. for 2 hours. Then, the Vero cells were gently washed with 200 μL TPA medium twice, and the virus-scFv mixtures or the controls were inoculated onto the cells in each well, respectively. The CPE of PEDV, which was expected as syncytial cells, was examined at 24, 48, and 72 hours after inoculation.

Example 1 Characterization of Recombinant scFv

The expression of the present scFv by EXPI293F™ was confirmed by western blotting with an anti-V5 tag antibody, in which a high level of expression of the scFv was observed (data not shown). The recombinant scFv was then purified by IMAC followed by SEC (data not shown), and verified by SDS-PAGE and commassie blue staining (data not shown). The SEC analysis indicated the presence of some aggregations formed by the recombinant scFv (data not shown), and the fractions corresponding to the main elution peak of scFv were collected for the following experiments.

Example 2 Binding Affinity of Recombinant scFv to Homogenous and Heterogeneous PEDV Virions by Immunostainings and ELISA The purified scFv was subjected to ICC and IFA to verify its binding affinity to PEDV virions. Vero cells were respectively infected by G1 PEDV (PEDV-CV777, the historic vaccine strain) and G2b PEDV (PEDV-PT passage 5 strain) followed by incubating with the recombinant scFv in accordance with the procedures described in Materials and Methods. The data indicated that the recombinant scFv was able to probe the PEDV-infected cells with obvious CPE as well as the peripherally scattered infected cells (data not shown). Despite being infected by the same titers, the morphologies of the cytopathic effects conferred by PEDV-CV777 and PEDV-PT strains were very different, in which the PEDV-PT formed small and scattered fusion cells, whereas PEDV-CV777 formed giant fusion cells (data not shown). Regardless of the cellular morphologies, the present scFv was capable of recognizing both G1 and G2b viruses (data not shown).

Figure 1:
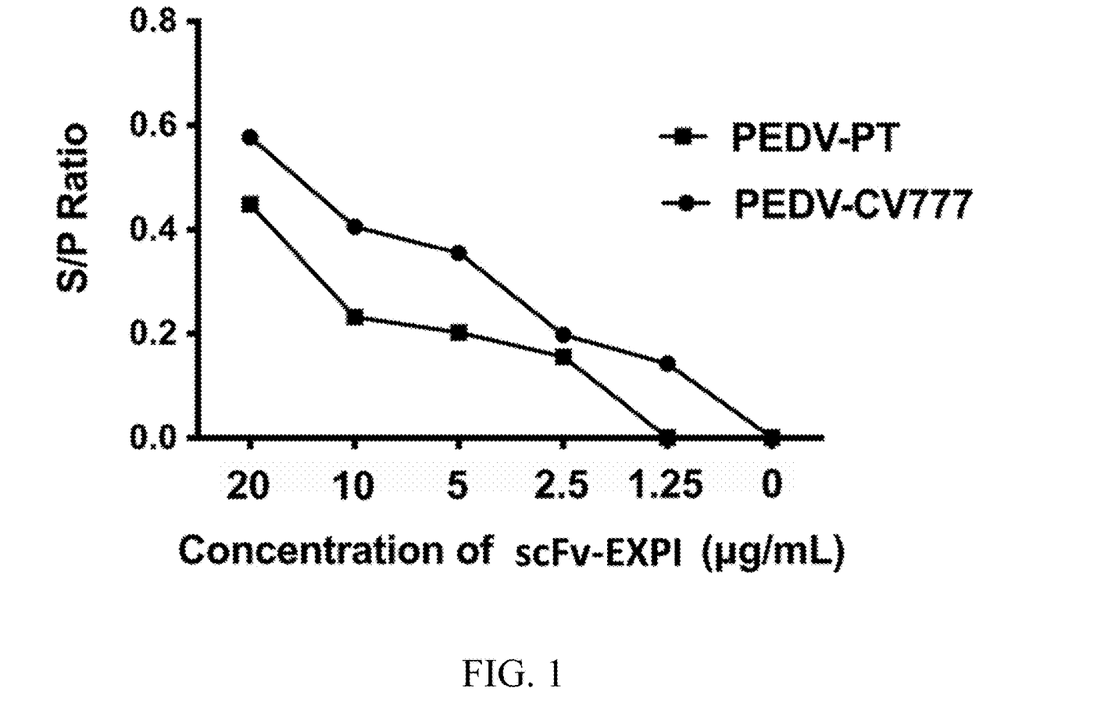
FIG. 1 is a line chart depicting the binding of the recombinant scFv toward PEDV virions according to Example 2 of the present disclosure. The virions of PEDV-PT (G2b PEDV) and PEDV-CV777 (G1 PEDV) were coated as the antigens on plates and probed with the serially-diluted scFv. The results were analyzed by enzyme-linked immunosorbent assay (ELISA). The S/P ratio was plotted as a function of scFv concentration.

The binding affinity of the present scFv against homogenous and heterogeneous PEDV was further estimated by ELISA. As the procedures described in Materials and Methods, both PEDV-PT and PEDV-CV777 virions were coated on the plates and incubated with different amounts of recombinant scFv. Another IgG antibody known to recognize PEDV was used as a positive control to calculate the sample-to-positive ratio (S/P ratio), which was defined as, $$S/P \text{ ratio} = \frac{OD_{sample} - OD_{negative\ control}}{OD_{positive\ control} - OD_{negative\ control}}$$

The S/P ratio for both viruses (i.e., PEDV-PT and PEDV-CV777) positively correlated with the concentration of scFv, indicating the cross-reactivity of the present scFv (FIG. 1).

Example 3 Binding Affinity of Recombinant scFv to Purified PEDV S Protein by Using Pull-Down Assay and SEC To further confirm that the PEDV S protein contains the epitope recognized by the present scFv, an immunoprecipitation combined pull-down assay and SEC analysis were performed in this example. For the immunoprecipitation assay, the purified trimeric PEDV S glycoprotein, which harbored a V5 tag and a His6 tag, was incubated with the recombinant scFv for 3 hours and size-filtrated by centrifugation with a 100 kDa molecular weight cut-off (MWCO) spin column. In the absence of the PEDV S protein, all scFv passed through the 100 kDa MWCO spin column in the control group, and no protein band was detected in the respective lane of the SDS-PAGE (data not shown). The addition of the PEDV S protein retained the scFv after the 100 kDa MWCO filtration (data not shown). The SEC analysis of the PEDV S protein with excess scFv showed a similar elution volume as that without scFv, potentially due to the relatively small change in molecular size of the PEDV S protein when bound to the scFv (data not shown). To ascertain that the scFv was indeed co-eluted with the PEDV S protein during the SEC, the elution fractions corresponding to the PEDV S protein were analyzed by western blotting. The data confirmed the binding between the present scFv and PEDV S protein (data not shown).

Example 4 Neutralizing Test

Figure 2:
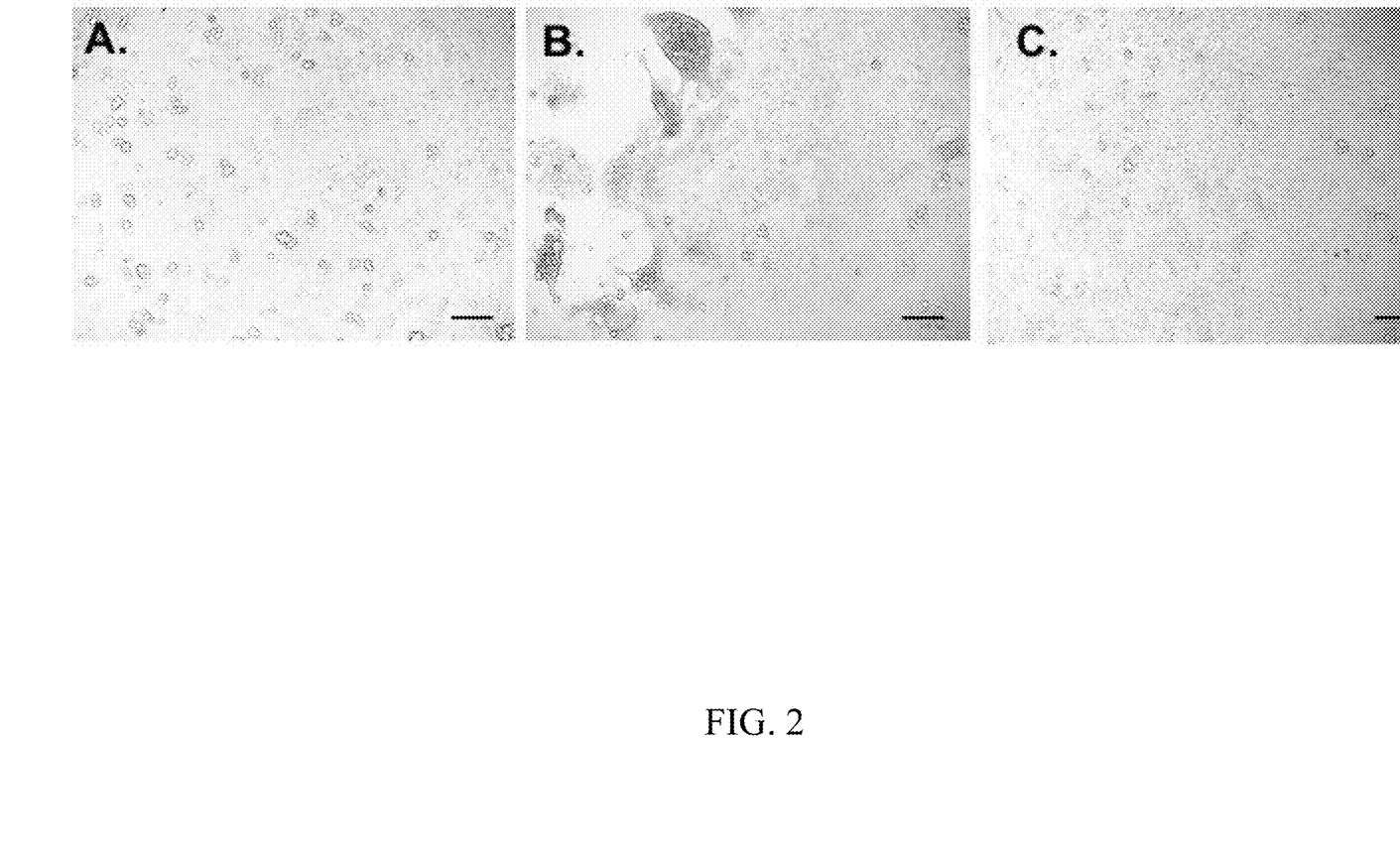

The neutralizing ability of scFv against virulent G2b PEDV (PEDV-PT) and G1 PEDV (PEDV-CV777) was evaluated by neutralization test and end-point cell viability test. The data indicated that the recombinant scFv was able to completely block the infection and the development of CPE of PEDV-PT-infected Vero cells, in which 6.25 μg/mL scFv was sufficient to block the PEDV-induced CPE at 24 hpi; 12.5 μg/mL scFv was sufficient to block the PEDV-induced CPE at 48 hpi; and the protection conferred by 25 μg/mL scFv lasted up to 72 hpi (FIG. 2, Table 3). As the data depicted in FIG. 2, at 72 hpi, no obvious CPE was observed in the non-challenged control group (Panel C) and in the group supplemented with 25 μg/mL scFv (Panel A) as compared to the severe CPEs observed in the challenged control group (Panel B). No detectable viral neutralizing ability of the present scFv against PEDV-CV777 was noted.

TABLE 3

The neutralizing ability of recombinant scFv against the G2b PEDV

| Time post challenge (hr) | Concentration of scFv (μg/mL) | Protection |
|---|---|---|
| 24 | 6.25 | No CPE |
|  | 12.5 | No CPE |
|  | 25 | No CPE |
| 48 | 6.25 | Few CPE |
|  | 12.5 | No CPE |
|  | 25 | No CPE |
| 72 | 6.25 | CPE |
|  | 12.5 | Few CPE |
|  | 25 | No CPE |

In conclusion, the inventors of the present invention identified a recombinant scFv, which recognized the S protein of G1 and G2b PEDV, and was capable of neutralizing the activity of G2b PEDV. Based on the binding and neutralizing activities, the present scFv provides a potential means to detect PEDV infection (e.g., G1 or G2b PEDV infection), and treat PEDV infection (e.g., G2b PEDV infection).

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A recombinant antibody comprising a light chain variable (VL) domain and a heavy chain variable (VH) domain, wherein the VL domain comprises a first light chain complementarity determining region (CDR-L1), a second light chain CDR (CDR-L2) and a third light chain CDR (CDR-L3), and the VH domain comprises a first heavy chain CDR (CDR-H1), a second heavy chain CDR (CDR-H2) and a third heavy chain CDR (CDR-H3), wherein
the CDR-L1, CDR-L2 and CDR-L3 respectively comprise the amino acid sequences of ENVGTY (SEQ ID NO: 1), GTF, and GQSYNYPFT (SEQ ID NO: 2); and
the CDR-H1, CDR-H2 and CDR-H3 respectively comprise the amino acid sequences of GYTFTNYM (SEQ ID NO: 3), INPSTGYT (SEQ ID NO: 4), and ATSTLITGDY (SEQ ID NO: 5).

2. The recombinant antibody of claim 1, wherein the VL domain comprises an amino acid sequence at least 85% identical to SEQ ID NO: 6, and the VH domain comprises an amino acid sequence at least 85% identical to SEQ ID NO: 7.

3. The recombinant antibody of claim 2, wherein the VL domain comprises an amino acid sequence 100% identical to SEQ ID NO: 6, and the VH domain comprises an amino acid sequence 100% identical to SEQ ID NO: 7.

4. The recombinant antibody of claim 1, wherein the recombinant antibody is a single-chain variable fragment (scFv).

5. The recombinant antibody of claim 4, further comprising a linker connecting the VL domain and the VH domain, wherein the linker comprises the amino acid sequence of (GGGGS)$_3$ (SEQ ID NO: 8).

6. A method of diagnosing whether a subject is infected by porcine epidemic diarrhea virus (PEDV) via a biological sample isolated from the subject, comprising detecting the presence or absence of a spike (S) protein of the PEDV in the biological sample by use of the recombinant antibody of claim 1, wherein the presence of the S protein indicates that the subject is infected by the PEDV.

7. The method of claim 6, wherein the PEDV is genotype 1 (G1) or genotype 2b (G2b) PEDV.

8. The method of claim 6, wherein the biological sample is a blood sample, an oral sample, an intestinal sample, a rectal sample or a fecal sample.

\* \* \* \* \*

SEQUENCE LISTING

```
<160> NUMBER OF SEQ ID NOS: 12

<210> SEQ ID NO 1
<211> LENGTH: 6
<212> TYPE: PRT
<213> ORGANISM: Artificial Sequence
<220> FEATURE:
<223> OTHER INFORMATION: synthesized_CDR-L1

<400> SEQUENCE: 1

Glu Asn Val Gly Thr Tyr
1               5

<210> SEQ ID NO 2
<211> LENGTH: 9
<212> TYPE: PRT
<213> ORGANISM: Artificial Sequence
<220> FEATURE:
<223> OTHER INFORMATION: synthesized_CDR-L3

<400> SEQUENCE: 2

Gly Gln Ser Tyr Asn Tyr Pro Phe Thr
1               5

<210> SEQ ID NO 3
<211> LENGTH: 8
<212> TYPE: PRT
<213> ORGANISM: Artificial Sequence
<220> FEATURE:
<223> OTHER INFORMATION: synthesized_CDR-H1

<400> SEQUENCE: 3
```

```
Gly Tyr Thr Phe Thr Asn Tyr Met
1               5
```

<210> SEQ ID NO 4
<211> LENGTH: 8
<212> TYPE: PRT
<213> ORGANISM: Artificial Sequence
<220> FEATURE:
<223> OTHER INFORMATION: synthesized_CDR-H2

<400> SEQUENCE: 4

```
Ile Asn Pro Ser Thr Gly Tyr Thr
1               5
```

<210> SEQ ID NO 5
<211> LENGTH: 10
<212> TYPE: PRT
<213> ORGANISM: Artificial Sequence
<220> FEATURE:
<223> OTHER INFORMATION: synthesized_CDR-H3

<400> SEQUENCE: 5

```
Ala Thr Ser Thr Leu Ile Thr Gly Asp Tyr
1               5                   10
```

<210> SEQ ID NO 6
<211> LENGTH: 132
<212> TYPE: PRT
<213> ORGANISM: Artificial Sequence
<220> FEATURE:
<223> OTHER INFORMATION: synthesized_VL domain

<400> SEQUENCE: 6

```
Met Asp Ala Met Lys Arg Gly Leu Cys Cys Val Leu Leu Leu Cys Gly
1               5                   10                  15

Ala Val Phe Val Ser Pro Ser Ala Ser Asn Ile Val Leu Thr Gln Ser
            20                  25                  30

Pro Lys Ser Met Ser Met Ser Val Gly Glu Arg Val Thr Leu Ser Cys
        35                  40                  45

Lys Ala Ser Glu Asn Val Gly Thr Tyr Val Ser Trp Tyr Gln Gln Lys
    50                  55                  60

Pro Lys Gln Ser Pro Lys Leu Leu Ile Tyr Gly Thr Phe Asn Arg Tyr
65                  70                  75                  80

Thr Gly Val Pro Asp Arg Phe Thr Gly Ser Gly Ser Ala Thr Asp Phe
                85                  90                  95

Thr Leu Thr Ile Ser Ser Val Gln Ala Glu Asp Leu Ala Asp Tyr His
            100                 105                 110

Cys Gly Gln Ser Tyr Asn Tyr Pro Phe Thr Phe Gly Ser Gly Thr Lys
        115                 120                 125

Leu Glu Ile Lys
    130
```

<210> SEQ ID NO 7
<211> LENGTH: 125
<212> TYPE: PRT
<213> ORGANISM: Artificial Sequence
<220> FEATURE:
<223> OTHER INFORMATION: synthesized_VH domain

<400> SEQUENCE: 7

```
Gln Val Gln Leu Gln Gln Ser Gly Ala Glu Leu Ala Arg Pro Gly Thr
1               5                   10                  15
```

-continued

Ser Val Lys Met Ser Cys Lys Ala Ser Gly Tyr Thr Phe Thr Asn Tyr
            20                  25                  30

Met Met His Trp Ile Lys Gln Arg Pro Gly Gln Gly Leu Glu Trp Ile
        35                  40                  45

Gly Tyr Ile Asn Pro Ser Thr Gly Tyr Thr Asn Tyr Asn Gln Lys Phe
    50                  55                  60

Lys Asp Lys Ala Thr Leu Thr Ala Asp Lys Ser Ser Thr Ala Tyr
65                  70                  75                  80

Val Gln Leu Asn Ile Leu Thr Ser Glu Asp Ser Ala Val Tyr Tyr Cys
                85                  90                  95

Ala Thr Ser Thr Leu Ile Thr Gly Asp Tyr Trp Gly Gln Gly Thr Thr
            100                 105                 110

Leu Thr Val Ser Ser Lys Gly Gln Asp Asn Ser Ala Gly
        115                 120                 125

<210> SEQ ID NO 8
<211> LENGTH: 15
<212> TYPE: PRT
<213> ORGANISM: Artificial Sequence
<220> FEATURE:
<223> OTHER INFORMATION: synthesized_linker

<400> SEQUENCE: 8

Gly Gly Gly Gly Ser Gly Gly Gly Gly Ser Gly Gly Gly Gly Ser
1               5                   10                  15

<210> SEQ ID NO 9
<211> LENGTH: 22
<212> TYPE: DNA
<213> ORGANISM: Artificial Sequence
<220> FEATURE:
<223> OTHER INFORMATION: synthesized_ISPCR

<400> SEQUENCE: 9
aagcagtggt atcaacgcag ag                                           22

<210> SEQ ID NO 10
<211> LENGTH: 24
<212> TYPE: DNA
<213> ORGANISM: Artificial Sequence
<220> FEATURE:
<223> OTHER INFORMATION: synthesized_mIgK reverse primer

<400> SEQUENCE: 10
acattgatgt ctttggggta gaag                                         24

<210> SEQ ID NO 11
<211> LENGTH: 20
<212> TYPE: DNA
<213> ORGANISM: Artificial Sequence
<220> FEATURE:
<223> OTHER INFORMATION: synthesized_mIgL reverse primer

<400> SEQUENCE: 11
atcgtacaca ccagtgtggc                                              20

<210> SEQ ID NO 12
<211> LENGTH: 20
<212> TYPE: DNA
<213> ORGANISM: Artificial Sequence
<220> FEATURE:
<223> OTHER INFORMATION: synthesized_mIgHG reverse primer -continued

```
<400> SEQUENCE: 12
gggatccaga gttccaggtc                                              20
```